United States Patent
Tournilhac et al.

(10) Patent No.: US 6,869,599 B2
(45) Date of Patent: Mar. 22, 2005

(54) COSMETIC COMPOSITION COMPRISING A PARTICLE DISPERSION

(75) Inventors: Florence Tournilhac, Paris (FR); Béatrice Toumi, Verrieres le Buisson (FR)

(73) Assignee: L'Oreal S.A., Paris (FR)

( * ) Notice: Subject to any disclaimer, the term of this patent is extended or adjusted under 35 U.S.C. 154(b) by 212 days.

(21) Appl. No.: 10/195,317

(22) Filed: Jul. 16, 2002

(65) Prior Publication Data

US 2003/0053976 A1 Mar. 20, 2003

Related U.S. Application Data

(60) Provisional application No. 60/306,416, filed on Jul. 20, 2001.

(30) Foreign Application Priority Data

Jul. 16, 2001 (FR) .............................. 01 09497

(51) Int. Cl.$^7$ ............................ A61K 7/025; A61K 7/48
(52) U.S. Cl. .............................. 424/64; 424/69; 424/65; 424/70.7; 424/401
(58) Field of Search .............................. 424/64, 69, 65, 424/70.7, 401, 63

(56) References Cited

U.S. PATENT DOCUMENTS

| | | |
|---|---|---|
| 5,650,159 A | 7/1997 | Lion et al. |
| 5,922,334 A | 7/1999 | Krasnansky et al. |
| 5,945,095 A | 8/1999 | Mougin et al. |
| 5,972,354 A | 10/1999 | de la Poterie et al. |
| 6,326,013 B1 | 12/2001 | Lemann et al. |
| 6,335,005 B1 | 1/2002 | Müller et al. |

FOREIGN PATENT DOCUMENTS

| | | |
|---|---|---|
| EP | 0 424 112 A2 | 4/1991 |

OTHER PUBLICATIONS

Patent Abstracts of Japan, vol. 016, No. 342 (C–0966), Jul. 24, 1992, JP 04 103510 A.

Masakazu Hirose et al., "The structure and properties of acrylic–polyurethane hybrid emulsions," Progress in Organic Coatings, vol. 38, 2000, pp. 27–34.

*Primary Examiner*—Jyothsna Venkat
(74) *Attorney, Agent, or Firm*—Finnegan, Henderson, Farabow, Garrett & Dunner, L.L.P.

(57) ABSTRACT

The invention relates to a cosmetic makeup composition and/or care composition for the skin and the lips, comprising a dispersion, in a cosmetically acceptable medium, of particles comprising at least one at least partially external supple phase comprising at least one supple polymer having at least one glass transition temperature of less than or equal to 60° C., and an at least partially internal rigid phase which is an amorphous material having a glass transition temperature of greater than 60° C., the supple polymer being at least partially attached by chemical grafting onto the rigid phase. The invention also relates to the use of such a particle dispersion to improve the comfort and staying power of cosmetic compositions.

83 Claims, No Drawings

COSMETIC COMPOSITION COMPRISING A PARTICLE DISPERSION

The present invention relates to a cosmetic composition, especially a makeup and/or care composition for the skin and the lips, comprising a dispersion of multiphase particles in a cosmetically acceptable medium. The invention also relates to a makeup process or care process for the skin and the lips.

The use of film-forming polymers as an aqueous dispersion in cosmetic compositions, as described, for example, in EP-A-0 775 483, makes it possible to increase the staying power of the composition applied to the skin. However, while these cosmetic compositions are drying on the skin, they often give rise to sensations of tautness that the user finds unpleasant, making the composition uncomfortable to wear. These problems of comfort are especially associated with the mechanical properties of the deposits obtained on the skin. In particular, when the film formed on the skin after applying the composition is too rigid, it leaves an unpleasant mask sensation, for example during movements of the face.

In addition, the film deposited on the skin may be damaged by rubbing with the fingers or fabrics (towels, handkerchiefs or clothing) and disintegrate: in this case, the film has poor staying power, especially poor resistance to rubbing.

Moreover, a cosmetic composition comprising polymer particles dispersed in an oily medium and surface-stabilized with a stabilizer that may be a block polymer, a polymer grafted with pendent chains, or a random polymer, is known from document EP-A-0 987 012. Such a composition has transfer-resistance properties. However, the stabilizer can be dissolved in the dispersion medium during storage of the composition in the jar or during its use, giving rise to instability of the composition, which is no longer homogeneous.

Moreover, when the cosmetic composition comprises a film-forming compound that forms a particularly supple film, the composition, after application to the skin, generally forms a sticky film, making the composition unpleasant for the user to apply, especially due to the sensation of a sticky surface effect when the composition is applied to the skin.

There is thus still a need for a stable cosmetic composition to be applied to the skin, which forms a deposit that is comfortable on the skin and that shows good staying power, especially good resistance to rubbing.

The inventors have discovered that such a composition may be obtained by using a dispersion of particular multiphase particles in a cosmetically acceptable medium.

Surprisingly, the Applicant has found that such a composition gives a deposit on the skin that shows noteworthy cosmetic properties. In particular, such a composition is comfortable to apply and shows good staying power, especially good resistance to rubbing. It has no surface stickiness and has very good mechanical qualities once applied to the skin, after drying. In addition, the composition is stable, i.e. there is no decomposition of the two rigid and supple phases of the particles, with respect to each other, thus avoiding the appearance, in the packaging or during or following the application of the composition, of macroscopic heterogeneous areas.

The advantage of the composition according to the invention is also that it has properties of absence of migration and of "transfer resistance". The term "migration" means an overflowing of the composition beyond the initial mark. Specifically, large migration of a cosmetic composition, and in general of the liquid fatty phase that may be present in said composition, in particular when it is charged with coloring materials, leads to an unattractive effect around the area of application, for example around the eyes, which particularly accentuates wrinkles and fine lines. The composition according to the invention thus makes it possible to limit, especially in hot and humid regions, the migration of a part of the composition into the wrinkles and fine lines, after it has been deposited on the skin. Furthermore, the composition according to the invention shows virtually no transfer, i.e. it virtually does not come off, leaving marks, on certain supports with which it may be placed in contact, and especially a glass, an item of clothing or the skin. Consequently, the user does not need to regularly freshen the application of the composition, especially of a foundation, and does not have to tolerate the appearance of these unacceptable marks, for example on blouse collars.

One subject of the invention is, precisely, a cosmetic composition, especially a makeup composition and/or care composition for the skin and the lips, comprising a dispersion of particles in a cosmetically acceptable medium, the particles comprising at least one at least partially external supple phase comprising at least one supple polymer having at least one glass transition temperature of less than or equal to 60° C., and at least one at least partially internal rigid phase, the rigid phase being an amorphous material having at least one glass transition temperature of greater than 60° C., the supple polymer being at least partially attached by chemical grafting onto the rigid phase.

The glass transition temperature corresponds to the temperature at which the amorphous material changes from a glassy solid state to a rubbery state. This temperature may be measured by differential thermal analysis (DTA) and differential calorimetry ("DSC" method, for "Differential Scanning Calorimetry"). In particular, the glass transition temperature may be measured by differential calorimetry (DSC) according to ASTM standard D3418-97.

The expression "cosmetically acceptable medium" means a medium that is compatible with keratin materials, for instance human skin.

The particles according to the invention, also known as multiphase particles (or composites), are particles comprising at least one supple phase and at least one rigid phase.

The supple polymer of the particles in dispersion has at least one glass transition temperature of less than or equal to 60° C., especially ranging from −120° C. to 60° C., preferably less than or equal to 45° C., especially ranging from −120° C. to 45° C. and preferentially less than or equal to 30° C., especially ranging from −120° C. to 30° C.

The supple polymer may be chosen from block polymers and/or random polymers. The expression "block polymers and/or random polymers" means polymers whose monomer distribution on the main chain or pendent chain members is in block and/or random form.

The supple polymer may be chosen from free-radical polymers, polycondensates and silicone polymers. The supple polymer may be chosen from polyacrylics, polymethacrylics, polyamides, polyurethanes, polyolefins, especially polyisoprenes, polybutadienes and polyisobutylenes (PIB), polyesters, polyvinyl ethers, polyvinylthio ethers, polyoxides, polysiloxanes and especially polydimethylsiloxanes (PDMS), and combinations thereof. The term "combinations" means copolymers that may be formed from monomers, leading to the formation of said polymers.

Preferably, the supple polymer may be chosen from poly(meth)acrylics, polyurethanes, polyolefins and polysiloxanes.

The amorphous material of the rigid phase has a glass transition temperature of greater than 60° C., especially greater than 60° C. and less than or equal to 200° C., preferably greater than or equal to 70° C., especially ranging from 70° C. to 200° C., in particular ranging from 70° C. to 150° C., and preferentially greater than or equal to 90° C., especially ranging from 90° C. to 150° C.

The amorphous material of the rigid phase may be a polymer, especially a block and/or random polymer. It may be a polymer chosen from polyacrylics, polymethacrylics such as, for example, poly((meth)acrylic acid), poly(meth)acrylamides, polyvinyls, polyvinyl esters, polyolefins, polystyrenes, polyvinyl halides, for instance polyvinyl chloride (PVC), polyvinylnitriles, polyurethanes, polyesters, polyamides, polycarbonates, polysulfones, polysulfonamides, polycyclics containing a carbon-based ring in the main chain, for instance polyphenylenes or polyoxyphenylenes, and combinations thereof.

Preferably, the amorphous material of the rigid phase may be a polymer chosen from polyacrylics, polymethacrylics such as, for example, poly((meth)acrylic acid), poly(meth)acrylamides, polyvinyls, polyvinyl esters, polyolefins, polystyrenes, polyvinyl halides, for instance polyvinyl chloride (PVC), polyvinylnitriles, polyurethanes, polyamides and polyesters.

According to one preferred embodiment of the invention, the supple and rigid phases of the multiphase particles may comprise at least one free-radical polymer obtained by, or even essentially by, polymerization of monomers chosen from the group formed by:
(meth)acrylic acid esters, for instance alkyl (meth)acrylates, especially containing a $C_1$–$C_8$ alkyl group,
vinyl esters of linear or branched carboxylic acids, such as vinyl acetate or vinyl stearate,
styrene and its derivatives, such as chloromethylstyrene or α-methylstyrene,
conjugated dienes, such as butadiene or isoprene,
acrylamide, methacrylamide and acrylonitrile,
vinyl chloride,
(meth)acrylic acid.

The selection of monomers (nature and content), which may be a single monomer or a mixture of at least two monomers, of the supple polymer and of the amorphous material of the rigid phase, is determined by the glass transition temperature that it is desired to give to each polymer.

The polymers of the rigid and/or supple phases may be crosslinked with monomers containing at least two copolymerizable double bonds, chosen, for example, from:
conjugated dienes, such as butadiene or isoprene;
allylic esters of α, β-unsaturated carboxylic acids, such as allyl acrylate or allyl methacrylate;
allylic esters of α, β-unsaturated dicarboxylic acids, such as diallyl maleate;
polyacrylics or polymethacrylics generally comprising at least two ethylenic unsaturations, such as ethylene glycol dimethacrylate, 1,3-butylene glycol dimethacrylate, 1,4-butanediol diacrylate or pentaerythritol tetraacrylate;
polyvinyls such as divinylbenzene or trivinylbenzene;
polyallylics such as triallyl cyanurate.

Said chemical grafting allows, by the formation of covalent bonds, stable bonding of the rigid phase and the supple phase of the multiphase particles.

The chemical grafting may be performed by block free-radical polymerization (also known as block polymerization) according to the procedures that are well known to those skilled in the art. The block polymerization consists, in a first step, in polymerizing the monomers of the rigid polymer (polymer forming the rigid phase of the particles) and then, in a second step, in continuing the polymerization with the monomers forming the supple polymer (polymer forming the supple phase of the particles). In this way, the polymer chains of the supple phase are at least partially linked by covalent bonding to the chains of the polymer of the rigid phase, the covalent bonding resulting from the polymerization of a monomer of the supple polymer with a monomer of the rigid polymer. Preferentially, the monomers of the polymer of the external supple phase have greater affinity for the dispersion medium than the monomers of the polymer of the internal rigid phase.

The supple polymer may be grafted onto the rigid polymer by means of a grafting monomer, said monomer possibly being a monomer containing several double bonds (ethylenic bonds), in particular a monomer containing two ethylenic double bonds. The grafting monomer may be a conjugated diene such as those described above or an allylic ester (especially diester) of α, β-unsaturated dicarboxylic acids such as those described above (such as, for example, diallyl maleate) which contain two polymerizable functions (ethylenic double bond) of different reactivity: one of the polymerizable functions (ethylenic double bond) of the grafting monomer is polymerized with the polymer of the amorphous material of the rigid phase (rigid polymer) and the other polymerizable function (ethylenic double bond) of the same grafting monomer is polymerized with the supple polymer.

When the supple polymer or the polymer of the rigid phase is a polycondensate, it is preferred to use a polycondensate containing at least one ethylenic unsaturation capable of reacting with a monomer also comprising an ethylenic unsaturation, to form a covalent bond with the polycondensate. Polycondensates comprising one or more ethylenic unsaturations are especially obtained by polycondensation of monomers such as allyl alcohol, vinylamine or fumaric acid. For example, vinyl monomers may be polymerized with a polyurethane containing vinyl groups in or at the end of the polyurethane chain, and may thus graft a vinyl polymer onto a polyurethane; a dispersion of particles of such a grafted polymer is especially described in the publications "The Structure and Properties of Acrylic-Polyurethane Hybrid Emulsions", Hiroze M., Progress in Organic Coatings, 38 (2000), pages 27–34; "Survey of the Applications, Properties, and Technology of Crosslinking Emulsions", Bufkin B, Journal of Coatings Technology, vol. 50, No. 647, December 1978.

The same grafting principle applies to silicones using silicones comprising vinyl groups, allowing vinyl monomers to be polymerized on the silicone and thus allowing vinyl polymer chains to be grafted onto a silicone.

In one embodiment of the invention, the particles containing rigid and supple phases are film-forming, and may have a minimum film-forming temperature (MFFT) of less than or equal to about 30° C. (especially ranging from −120° C. to 30° C.), preferably less than or equal to about 25° C. (especially ranging from −120° C. to 25° C.); the particles containing rigid and supple phases may thus form a film at a temperature of about 30° C.

The particles containing rigid and supple phases generally have a size ranging from 1 nm to 10 μm and preferably ranging from 10 nm to 1 μm. The particle size may be measured, for example, using a Brookhaven BI-90 machine by the technique of light scattering, or with a Malvern Mastersizer 2000 granulometer, or alternatively by electron microscopy.

The supple phase may be present in the particles in a content of at least 1% by volume, relative to the total volume of the particle, preferably at least 5% by volume, preferentially at least 10% by volume and even more preferably at least 25% by volume, and up to 99.999% by volume, preferably up to 99.9% by volume, preferentially up to 99% by volume and more preferentially up to 95% by volume, and in particular ranging from 1% to 99.999% by volume, preferably ranging from 5% to 99.9% by volume, especially ranging from 10% to 99.9% by volume, preferentially ranging from 25% to 99.9% by volume and even more preferably ranging from 50% to 95% by volume, or even ranging from 50% to 90% by volume.

In any case, the rigid phase and the supple phase are incompatible, i.e. they can be distinguished using the techniques that are well known to those skilled in the art, such as, for example, the technique of observation by electron microscopy or the measurement of several glass transitions of the particles by differential calorimetry. The multiphase particles are thus inhomogeneous particles.

The morphology of the supple and rigid phases of the dispersed particles may be, for example, of core-shell type, with shell portions completely surrounding the core, but also of core-shell type with a plurality of cores, or an interpenetrating network of phases. In the multiphase particles, the supple phase is at least partly and preferably predominantly external, and the rigid phase is at least partly and preferably predominantly internal.

The multiphase particles may be prepared by consecutive series of polymerization, with different types of monomers. The particles of a first family of monomers are generally prepared in a separate step, or formed in situ by polymerization. Next, or at the same time, at least one other family of other monomers are polymerized during at least one additional polymerization step. The particles thus formed have at least one at least partially internal structure, or core, and at least one at least partially external structure, or shell. The formation of a "multilayer" heterogeneous structure is thus possible. A wide variety of morphologies may flow therefrom, of the core-shell type, but also, for example, with fragmented inclusions of the rigid phase in the supple phase. According to the invention, it is essential for the structure as an at least partially external supple phase to be more supple than the structure as an at least partially internal rigid phase.

The multiphase particles present in the composition according to the invention are in dispersion in a physiologically acceptable medium.

According to a first embodiment of the invention, the multiphase particles may be dispersed in an aqueous medium, especially a hydrophilic medium. The aqueous medium may consist predominantly of water, and preferably virtually totally of water. These dispersed particles thus form an aqueous polymer dispersion, generally known as a latex or pseudolatex. The term "latex" means an aqueous dispersion of polymer particles as may be obtained by emulsion polymerization of at least one monomer.

The dispersion of multiphase particles is generally prepared by at least one emulsion polymerization, in an essentially aqueous continuous phase, using reaction initiators, such as photochemical or thermal initiators for a free-radical polymerization, optionally in the presence of additives such as stabilizers, chain-transfer agents and/or catalysts.

The aqueous medium may comprise, in addition to water, a water-miscible solvent, for instance polyols, especially polyols containing from 2 to 8 carbon atoms (for example glycerol, diglycerol or ethylene glycol), $C_2$–$C_5$ lower monoalcohols (for example ethanol or isopropanol), $C_2$–$C_4$ ketones (for example acetone or diacetone), and mixtures thereof. The aqueous medium can represent from 5% to 75% by weight and better still from 5% to 50% by weight relative to the total weight of the composition.

According to a second embodiment of the invention, the multiphase particles may be dispersed in a lipophilic medium, i.e. a nonaqueous medium, especially a nonaqueous medium that is liquid at room temperature (25° C.) and atmospheric pressure.

In this case, the particles are generally prepared by at least one solution polymerization, in a solvent or organic medium, using reaction initiators, such as free-radical thermal initiators, for an essentially free-radical polymerization. The chosen solvent phase must allow the monomers to be dissolved but it must no longer be a solvent for the final polymer, which ends up in dispersion. The compounds generally present for such a preparation may be stabilizers, chain-transfer agents and/or catalysts.

The lipophilic medium may comprise a cosmetically or dermatologically acceptable oil, and more generally a physiologically acceptable oil, chosen especially from carbon-based oils, hydrocarbon-based oils, fluoro oils and/or silicone oils of mineral, animal, plant or synthetic origin, alone or as a mixture provided that they form a stable, homogeneous mixture and that they are compatible with the intended use. The oil may be a nonvolatile oil or a volatile oil, and preferably a volatile oil. The composition may also comprise a liquid fatty phase, without this phase comprising a polymer, and especially polymer particles as described above.

As oil that may be used in the invention, mention may thus be made of hydrocarbon-based oils such as liquid paraffin or liquid petroleum jelly, mink oil, turtle oil, soybean oil, perhydrosqualene, sweet almond oil, beauty-leaf oil, palm oil, grapeseed oil, sesame seed oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl alcohol or linolenyl alcohol, isostearyl alcohol or octyldodecanol; silicone oils such as polydimethylsiloxanes (PDMS), which are optionally phenylated such as phenyltrimethicones, or optionally substituted with aliphatic and/or aromatic groups that are optionally fluorinated, or with functional groups such as hydroxyl, thiol and/or amine groups; polysiloxanes modified with fatty acids, with fatty alcohols or with polyoxyalkylenes, fluorosilicones and perfluoro oils.

The composition according to the invention may comprise one or more oils that are volatile at room temperature. The expression "volatile oil" means any nonaqueous medium capable of evaporating from the skin or the lips or fibers, at room temperature. This volatile phase in particular comprises oils with a vapor pressure at room temperature and at atmospheric pressure ranging from 0.13 Pa to 40 000 Pa ($10^{-3}$ to 300 mm Hg). These volatile oils especially facilitate the application of the composition to the skin. These oils may be hydrocarbon-based oils, silicone oils (optionally comprising alkyl or alkoxy groups that are pendant or at the end of a silicone chain), and fluoro oils.

As volatile silicone oil, mention may be made of linear or cyclic silicones containing from 2 to 7 silicon atoms, these silicones optionally comprising alkyl or alkoxy groups containing from 1 to 10 carbon atoms. Mention may thus be made especially of octamethylcyclotetrasiloxane, decamethylcyclopenta-siloxane, hexadecamethylcyclohexasiloxane, heptamethylhexyltrisiloxane and heptamethyloctyltrisiloxane, and mixtures thereof.

Volatile hydrocarbon-based oils that may be mentioned include $C_8$–$C_{16}$ isoparaffins such as the Isopar and Permetyl products, and especially isododecane, isooctane, isodecane and isohexadecane, and mixtures thereof.

The composition may comprise represents especially from 5% to 97.5% by weight, relative to the total weight of the composition, and better still from 20% to 75% by weight, of oil and especially of volatile oil.

According to the invention, the lipophilic medium (or nonaqueous medium) described above may constitute a continuous phase of the composition or a phase dispersed in a continuous aqueous phase containing water and optionally water-soluble or water-miscible solvents such as those described above.

The multiphase particles may be present in the composition in a content ranging from 0.1% to 70% by weight of particle solids, relative to the total weight of the composition, preferably ranging from 0.5% to 55% by weight and preferentially ranging from 1% to 40% by weight.

Advantageously, the composition according to the invention is capable of forming a film that has a maximum tensile stress (for a percentage of elongation of less than 100%) of less than or equal to about 10 MPa (especially ranging from 0.1 MPa to 10 MPa) and preferably less than or equal to about 5 MPa (especially ranging from 0.1 MPa to 5 MPa). The maximum tensile stress may be determined during tensile tests as described in ASTM standard D638-99, for example on a dumbbell-shaped specimen with a working length of 33 mm and a width of 6 mm (of type IV according to the standard) at a speed of 50 mm/min. The specimens are cut into films about 100 μm thick (thickness after drying). To produce a film, the dispersions are poured into a Teflon-coated matrix, they are left to dry at a temperature equal to 25° C. in order for the volatile medium to evaporate off, and the film formed is recovered. The tests are preferentially performed on films that have been dried for at least 24 hours and better still 7 days at room temperature (25° C.) and at ambient humidity (50%).

Such a film has no surface stickiness, i.e. after contact between the finger and the surface of the film, no impression of stickiness of the surface is experienced when the contact is broken therewith by removing the finger, unlike the sensation that may be experienced after contact with an adhesive face, for example an adhesive tape.

The composition according to the invention may comprise an auxiliary film-forming agent to allow the formation of a film of the multiphase particles according to the invention at room temperature. The auxiliary agent may be a coalescer or a plasticizer known to those skilled in the art. A plasticizer is generally an organic compound that remains in the composition during the formation of the film. A coalescer is generally a volatile organic compound that evaporates off during the formation of the film.

The composition according to the invention may also comprise at least one dyestuff. The dyestuff may be chosen from the lipophilic dyes, hydrophilic dyes, pigments and nacres usually used in cosmetic or dermatological compositions, and mixtures thereof, all these compounds usually being used in cosmetic or dermatological compositions. The dyestuff is generally present in a proportion of from 0.01% to 50% by weight relative to the total weight of the composition, and referably from 1% to 30% by weight.

The liposoluble dyes are, for example, Sudan red, D&C Red 17, D&C Green 6, β-carotene, soybean oil, Sudan brown, D&C Yellow 11, D&C Violet 2, D&C Orange 5, quinoline yellow and annatto, or mixtures thereof.

The pigments may be white or colored, mineral and/or organic, coated or uncoated, and of usual or nanometric size. The term "pigments" should be understood as meaning particles that are insoluble in the medium, intended to color and/or opacify the composition. Among the mineral pigments that may be mentioned are titanium dioxide, optionally surface-treated, zirconium oxide or cerium oxide and also iron oxide or chromium oxide, manganese violet, ultramarine blue, chromium hydrate and ferric blue, and mixtures thereof. Among the organic pigments that may be mentioned are carbon black, pigments of D&C type, and lakes based on cochineal carmine or on barium, strontium, calcium or aluminum, and mixtures thereof. The pigments may especially be coated with at least one silicone compound such as polydimethylsiloxanes and/or with polymers, especially polyetheylenes and/or at least one fluoro compound and/or at least one amino acid. Mention may also be made of "SI oxides" which are polymethylhydrogenosiloxane-coated pigments sold by the company Miyoshi.

The nacreous pigments may be chosen from white nacreous pigments such as mica coated with titanium or with bismuth oxychloride, colored nacreous pigments such as titanium mica with iron oxides, titanium mica with, especially, ferric blue or chromium oxide, titanium mica with an organic pigment of the abovementioned type, and also nacreous pigments based on bismuth oxychloride, and mixtures thereof.

The composition may also contain at least one filler, especially in order to obtain a matt product, which is especially desired for foundations and in particular for foundations or day creams for individuals with greasy skin. The term "filler" means any particle that is solid at room temperature and atmospheric pressure, used alone or in combination, which does not react chemically with the various ingredients of the composition and which are insoluble in these ingredients, even when these ingredients are brought to a temperature above room temperature and especially to their softening point or to their melting point. These inert fillers have melting points at least higher than 170° C. and better still higher than 200° C. They may be absorbent or nonabsorbent, i.e. capable in particular of absorbing the oils of the composition and also the biological substances secreted by the skin. Preferably, these fillers have an apparent diameter ranging from 0.01 to 150 μm, preferably from 0.5 to 120 μm and better still ranging from 1 to 80 μm. An apparent diameter corresponds to the diameter of the circle in which the elementary particle is inscribed along its smallest dimension (thickness for lamellae)

The fillers that may be used in the composition according to the invention may be mineral or organic, lamellar, spherical or oblong. Mention may be made of talc, mica, silica, kaolin, polyamide powders, for instance Nylon® (Orgasol® from Atochem), poly-β-alanine powders, polyethylene powders, powders of an acrylic polymer and especially of polymethyl methacrylate (PMMA), for instance the product sold by Wackherr under the reference Covabead LH-85 (particle size 10–12 μm), powders of acrylic acid copolymers (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), carbonates such as precipitated calcium carbonate, magnesium carbonate and magnesium hydrocarbonate, hydroxyapatite, hollow silica microspheres (Silica Beads® from Maprecos), glass microcapsules, ceramic microcapsules and polyester particles, and mixtures thereof. These fillers may be surface-treated, especially to make them lipophilic.

The composition may optionally contain one or more waxes. For the purposes of the present invention, a wax is a lipophilic fatty compound, which is solid at room temperature (25° C.) with a reversible solid/liquid change of state, having a melting point of greater than 45° C. and better still greater than 55° C., which may be up to 200° C., and having in the solid state an anisotropic crystal organization. For the purposes of the patent application, the waxes are those generally used in cosmetics and dermatology; they are especially of natural origin, for instance beeswax, carnauba wax, candelilla wax, ouricoury wax, Japan wax, cork fiber wax or sugar cane wax, paraffin wax, lignite wax, microcrystalline waxes, lanolin wax, montan wax, ozokerites and hydrogenated oils, for instance hydrogenated jojoba oil, and also of synthetic origin, for instance polyethylene waxes derived from the polymerization of ethylene, waxes obtained by Fischer-Tropsch synthesis, esters of fatty acids and of glycerides that are solid at 40° C., and silicone waxes, for instance alkyl, alkoxy, and/or esters of poly(di)methylsiloxane that are solid at 40° C. Waxes of synthetic origin are preferably used for reasons of greater reproducibility than waxes of natural origin.

The composition according to the invention also advantageously contains at least one fatty compound that is pasty at room temperature. For the purposes of the invention, the expression "pasty fatty substance" means a compound with a melting point ranging from 25 to 60° C. and preferably from 30 to 45° C. and/or a hardness ranging from 0.001 to 0.5 MPa and preferably from 0.005 to 0.4 MPa.

The melting point values correspond to the melting point measured using a differential scanning calorimeter (DSC), such as the calorimeter sold under the name DSC 2920 by the company TA Instruments, with a temperature rise of 5 or 10° C. per minute. (The melting point considered is the point corresponding to the temperature of the most endothermic peak in the thermogram).

The hardness is measured according to a method of penetration of a probe into a sample of compound and in particular using a texture analyzer (for example the TA-XT2i from Rheo) equipped with a stainless steel cylinder 2 mm in diameter. The hardness measurement is performed at 20° C. at the center of 5 samples. The cylinder is introduced into each sample at a pre-speed of 1 mm/sec and then at a measuring speed of 0.1 mm/sec, the depth of penetration being 0.3 mm. The hardness value recorded is that of the maximum peak of the applied force.

According to the invention, one or more pasty fatty substances may also be used. Preferably, these fatty substances are hydrocarbon-based compounds, optionally of polymeric type; they may also be chosen from hydrocarbon-based compounds, silicone compounds and/or fluoro compounds, and mixtures thereof.

Among the pasty compounds that may be mentioned are lanolins and lanolin derivatives, for instance acetylated lanolins or oxypropylenated lanolins, with a viscosity from 18 to 21 Pa.s and preferably 19 to 20.5 Pa.s, and/or a melting point from 30 to 45° C., and mixtures thereof. Esters of fatty acids or of fatty alcohols may also be used, especially those containing 20 to 65 carbon atoms (melting point of about 20 to 35° C. and/or viscosity at 40° C. ranging from 0.1 to 40 Pa.s), for instance triisostearyl or cetyl citrate; arachidyl propionate; polyvinyl laurate; cholesterol esters, for instance triglycerides of plant origin such as hydrogenated plant oils, viscous polyesters, for instance poly(12-hydroxystearic acid), and mixtures thereof. Triglycerides of plant origin that may be used include hydrogenated castor oil derivatives, such as "Thixinr" from Rheox.

Mention may also be made of silicone pasty fatty substances such as polydimethylsiloxanes (PDMS) containing pendant chains of the alkyl or alkoxy type containing from 8 to 24 carbon atoms, and having a melting point of 20–55° C., for instance stearyl dimethicones, especially those sold by the company Dow Corning under the trade names DC2503 and DC25514, and mixtures thereof.

The pasty fatty substance may be present in a proportion of from 0.1% to 60% by weight, relative to the total weight of the composition, preferably in a proportion of from 1% to 45% by weight and even more preferentially in a proportion of from 2% to 30% by weight, in the composition.

The composition according to the invention may contain a surfactant or a mixture of surfactants, especially a surfactant whose HLB (hydrophilic/lipophilic balance) value allows the production of a water-in-oil (W/O) or oil-in-water (O/W) emulsion.

As surfactants that may be used, suitable for obtaining a W/O emulsion, mention may be made of those with an HLB value of less than 7, and especially fatty acid esters of polyols, for instance mono-, di-, tri- or or sesquioleates or stearates of sorbitol or of glycerol, glyceryl laurate or polyethylene glycol laurate; alkyl or alkoxy dimethicone copolyols with an alkyl or alkoxy chain pendant or at the end of the silicone skeleton, containing, for example, from 6 to 22 carbon atoms.

As surfactants that may be used to obtain an O/W emulsion, mention may be made of those with an HLB value of greater than 7, for instance fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers and dimethicone copolyols; and mixtures thereof. In general, any amphoteric ionic (cationic or anionic) surfactant and any nonionic surfactant that is well known to those skilled in the art may be used.

The composition of the invention may also comprise any additive usually used in the field under consideration, chosen especially from antioxidants, essential oils, preserving agents, fragrances, neutralizers, polymers that are liposoluble or dispersible in the medium, cosmetic or dermatological active agents such as, for example, emollients, moisturizers, vitamins, essential fatty acids, sunscreens, free-radical scavengers, dispersants, for instance poly(12-hydroxystearic acid), and mixtures thereof. These additives may be present in the composition in a proportion of from 0.01% to 30% and better still from 0.01% to 10% by weight relative to the total weight of the composition. Advantageously, the composition contains at least one cosmetic or dermatological active agent.

Needless to say, a person skilled in the art will take care to select the optional additional additives and/or the amount thereof such that the advantageous properties of the composition according to the invention are not, or are not substantially, adversely affected by the envisaged addition.

According to the invention, the composition according to the invention may be in the form of a simple or multiple emulsion containing an oily or aqueous continuous phase, an oily dispersion in an aqueous phase comprising vesicles containing ionic and/or nonionic lipids, a suspension, dispersion or solution in water or an aqueous-alcoholic medium, a mousse, or a dispersion of vesicles, especially of ionic or nonionic lipids.

The composition may have the appearance of a cream, a gel, a paste, a solid (especially a stick), a solid emulsion cast in a mold in the shape of a dish, an aqueous or aqueous-alcoholic gel, a hydrophilic mousse, an emulsified gel, a two-phase or multiphase lotion, or a spray.

A person skilled in the art can select the appropriate presentation form, and also the method for preparing it, on the basis of his general knowledge, taking into account on the one hand the nature of the constituents used, especially their solubility in the support, and on the other hand the intended use of the composition.

The composition according to the invention may be a lip makeup product such as a lipstick, a lip gloss or a lip pencil, or alternatively a lipcare product.

The composition may also be a skin makeup product (especially a colored product), for both the human face and body, in particular a foundation, optionally having care or treatment properties, a blusher, a face powder, an eye shadow, a concealer product, an eyeliner or a body makeup product, for instance temporary tattoo products. More especially, the composition according to the invention is a foundation, lipstick, eyeliner, eye shadow or face powder composition.

The composition according to the invention may also be in the form of a care composition and/or treatment composition for the skin (especially a dermatological composition), including the scalp, especially for facial and/or body skin. The skincare composition may be a skincare base, an antisun composition or a body hygiene composition, for instance deodorant products. The skincare composition may be a tinted composition.

A subject of the invention is also a cosmetic care process and/or makeup process for the skin and/or the lips, especially for human skin and/or human lips, comprising the application to the skin and/or the lips of a cosmetic composition as defined above.

A subject of the invention is also the use, in a cosmetic composition, of a dispersion of particles comprising at least one at least partially external supple phase comprising at least one supple polymer having at least one glass transition temperature of less than or equal to 60° C., and at least one at least partially internal rigid phase, the rigid phase being an amorphous material having at least one glass transition temperature of greater than 60° C., the supple polymer being at least partially attached by chemical grafting onto the rigid phase, to improve the staying power and comfort of a film of the composition applied to the skin, the particles being dispersed in a cosmetically acceptable medium.

A subject of the invention is also the use, in a cosmetic composition, of a dispersion of particles comprising at least one at least partially external supple phase comprising at least one supple polymer having a glass transition temperature of less than or equal to 60° C., and at least one at least partially internal rigid phase, the rigid phase being an amorphous material having at least one glass transition temperature of greater than 60° C., the supple polymer being at least partially attached by chemical grafting onto the rigid phase, the particles being dispersed in a cosmetically acceptable medium, to reduce the transfer and/or deposition of marks from a film of said composition, applied to the skin, onto a support placed in contact with said film.

The invention is illustrated in greater detail in the following example of a foundation. The percentages are given as mass percentages.

EXAMPLE 1 a) A latex of core/shell structure formed from 10% by weight, relative to the total weight of polymer particles, of internal rigid phase (core) formed from 100% by weight of methyl methacrylate (weight % relative to the total weight of the rigid phase), and from 90% by weight, relative to the total weight of polymer particles, of external supple phase formed from 50% by weight of n-butyl acrylate, 45% by weight of methyl methacrylate and 5% by weight of methacrylic acid (weight % expressed relative to the total weight of the supple phase) is prepared.

The supple phase has a glass transition temperature of about 10° C. and the rigid phase has a glass transition temperature of about 100° C. The multiphase particles comprise 10% by weight of internal rigid phase and 90% by weight of external supple phase (weight % relative to the total weight of the polymer particles).

This latex is prepared in two sequential polymerization steps:

In a first step, the methyl methacrylate and potassium persulfate dissolved to 0.4% in water are introduced into an aqueous solution containing 4% by weight of sodium lauryl sulfate, with stirring in a reactor heated to 80° C.; the mixture is left stirring for 30 minutes. Next, sodium bisulfite is added in a sodium bisulfite/potassium persulfate weight ratio of 1/4, dissolved in a minimum amount of water. The mixture is left to react for 1 hour.

In a second step, the mixture of n-butyl acrylate, methyl methacrylate and methacrylic acid (50/45/5 weight mixture) is added to the polymer emulsion obtained at the end of the first step, over 30 minutes, followed by simultaneous addition over 5 minutes of potassium persulfate dissolved to 0.1% in water. Next, sodium bisulfite is added in an added sodium bisulfite/added potassium persulfate weight ratio equal to 1/2 and the mixture is reacted for 3 hours at 80° C., then cooled to room temperature (25° C.) and the concentration of the polymer particles is adjusted to obtain a polymer solids content of 35% by weight.

This latex forms a film which has a maximum stress, as defined above, of strictly less than 5 MPa.

b) a foundation having the composition below is prepared:

| | |
|---|---|
| latex according to a) | 20% AM |
| pigments | 7% |
| dispersant (sold under the trade name Tamol 731DP by the company Rohm & Haas) | 0.02% |
| water | qs 100% |

After applying the makeup to the skin, the foundation has noteworthy staying-power and transfer-resistance properties, and is comfortable for the user to wear.

What is claimed is:

1. A cosmetic composition comprising a dispersion of particles in a cosmetically acceptable medium, said particles comprising at least one at least partially external supple phase comprising at least one supple polymer having at least one glass transition temperature of less than or equal to 60° C., and at least one at least partially internal rigid phase, said rigid phase being at least one amorphous material having at least one glass transition temperature of greater than 60° C., said at least one supple polymer being at least partially attached by chemical grafting onto said rigid phase.

2. A composition according to claim 1, wherein said at least one supple polymer has a glass transition temperature ranging from −120° C. to 60° C.

3. A composition according to claim 1, wherein said at least one supple polymer has a glass transition temperature of less than or equal to 45° C.

4. A composition according to claim 1, wherein said at least one supple polymer has a glass transition temperature ranging from −120° C. to 45° C.

5. A composition according to claim 1, wherein said at least one supple polymer has a glass transition temperature of less than or equal to 30° C.

6. A composition according to claim 1, wherein said at least one supple polymer has a glass transition temperature ranging from −120° C. to 30° C.

7. A composition according to claim 1, wherein said at least one supple polymer is chosen from polyacrylics, polymethacrylics, polyamides, polyurethanes, polyolefins, polyesters, polyvinyl ethers, polyvinylthio ethers, polyoxides, polysiloxanes, and combinations thereof.

8. A composition according to claim 1, wherein said at least one supple polymer is chosen from polyacrylics, polymethacrylics, polyurethanes, polyolefins and polysiloxanes.

9. A composition according to claim 1, wherein said at least one amorphous material of said rigid phase has a glass transition temperature of greater than 60° C. and less than or equal to 200° C.

10. A composition according to claim 1, wherein said at least one amorphous material of said rigid phase has a glass transition temperature of greater than or equal to 70° C.

11. A composition according to claim 1, wherein said at least one amorphous material of said rigid phase has a glass transition temperature ranging from 70° C. to 200° C.

12. A composition according to claim 1, wherein said at least one amorphous material of said rigid phase has a glass transition temperature of greater than or equal to 90° C.

13. A composition according to claim 1, wherein said at least one amorphous material of said rigid phase has a glass transition temperature ranging from 90° C. to 150° C.

14. A composition according to claim 1, wherein said at least one amorphous material of said rigid phase is a polymer.

15. A composition according to claim 1, wherein said at least one amorphous material of said rigid phase is a polymer chosen from polyacrylics, polymethacrylics, poly(meth)acrylamides, polyvinyls, polyvinyl esters, polyolefins, polystyrenes, polyvinyl halides, polyvinylnitriles, polyurethanes, polyesters, polyamides, polycarbonates, polysulfones, polysulfonamides, polycyclics containing a carbon-based ring in the main chain, polyoxyphenylenes, and combinations thereof.

16. A composition according to claim 1, wherein said at least one amorphous material of said rigid phase is a polymer chosen from polyacrylics, polymethacrylics, poly(meth)acrylamides, polyvinyls, polyvinyl esters, polyolefins, polystyrenes, polyvinyl halides, polyvinylnitriles, polyurethanes, polyamides and polyesters.

17. A composition according to claim 1, wherein one or both of said supple and rigid phases of said particles comprise at least one free-radical polymer obtained by polymerization of monomers chosen from alkyl (meth)acrylates containing a $C_1$–$C_8$ alkyl group, vinyl esters of linear or branched carboxylic acids, styrene and its derivatives, conjugated dienes, acrylamide, methacrylamide, acrylonitrile, vinyl chloride, and (meth)acrylic acid.

18. A composition according to claim 1, wherein one or both of said rigid and supple phases comprise a polymer crosslinked using a monomer containing at least two copolymerizable double bonds.

19. A composition according to claim 18, wherein said polymer is crosslinked with a monomer chosen from at least one of conjugated dienes, allylic esters of α,β-unsaturated carboxylic acids, allylic esters of α,β-unsaturated dicarboxylic acids, polyacrylics or polymethacrylics generally comprising at least two ethylenic unsaturations, polyvinyls and polyallylics.

20. A composition according to claim 18, wherein said polymer is crosslinked with a monomer chosen from butadiene, isoprene, allyl acrylate, allyl methacrylate, diallyl maleate, ethylene glycol dimethacrylate, 1,3-butylene glycol dimethacrylate, 1,4-butanediol diacrylate, pentaerythritol tetraacrylate, divinylbenzene, trivinylbenzene and triallyl cyanurate.

21. A composition according to claim 19, wherein said polymer is crosslinked with a monomer chosen from at least one of butadiene, isoprene, allyl acrylate, allyl methacrylate, diallyl maleate, ethylene glycol dimethacrylate, 1,3-butylene glycol dimethacrylate, 1,4-butanediol diacrylate, pentaerythritol tetraacrylate, divinylbenzene, trivinylbenzene and triallyl cyanurate.

22. A composition according to claim 1, wherein said rigid and supple phases comprise a polymer crosslinked using a monomer containing at least two copolymerizable double bonds.

23. A composition according to claim 22, wherein said supple phase comprise a polymer crosslinked using a monomer containing at least two copolymerizable double bonds.

24. A composition according to claim 22, wherein said rigid phase comprise a polymer crosslinked using a monomer containing at least two copolymerizable double bonds.

25. A composition according to claim 1, wherein said chemical grafting is formed by covalent bonding of said rigid phase and of said supple phase of said particles.

26. A composition according to claim 1, wherein said at least one amorphous material of said rigid phase is a polymer and said chemical grafting is performed by block free-radical polymerization.

27. A composition according to claim 1, wherein said at least one amorphous material of said rigid phase is a polymer and said chemical grafting is by a grafting monomer.

28. A composition according to claim 27, wherein said grafting monomer is a monomer containing two ethylenic double bonds.

29. A composition according to claim 27, wherein said grafting monomer is chosen from conjugated dienes and allylic esters of α,β-unsaturated dicarboxylic acids.

30. A composition according to claim 28, wherein said grafting monomer is chosen from conjugated dienes and allylic esters of α,β-unsaturated dicarboxylic acids.

31. A composition according to claim 1, wherein said at least one supple polymer or said rigid phase, if said rigid phase is a polymer, is a polycondensate containing at least one ethylenic unsaturation capable of reacting with a monomer also comprising an ethylenic unsaturation to form a covalent bond with the polycondensate.

32. A composition according to claim 31, wherein said polycondensate comprising at least one ethylenic unsaturation is obtained by polycondensation of monomers chosen from allyl alcohol, vinylamine and fumaric acid.

33. A composition according to claim 1, wherein said particles comprising rigid and supple phases are film-forming.

34. A composition according to claim 33, wherein said particles have a minimum film-forming temperature of less than or equal to 30° C.

35. A composition according to claim 33, wherein said particles have a minimum film-forming temperature from −120° C. to 30° C.

36. A composition according to claim 1, wherein said particles have a size from 1 nm to 10 μm.

37. A composition according to claim 36, wherein said particles have a size from 10 nm to 1 μm.

38. A composition according to claim 1, wherein said supple phase is present in said particles in a content of at least 1% by volume, relative to the total volume of the particle.

39. A composition according to claim 1, wherein said supple phase is present in said particles in a content from 1% to 99.999% or less, relative to the total volume of the particle.

40. A composition according to claim 1, wherein said supple phase is present in said particles in a content of at least 5% by volume, relative to the total volume of the particle.

41. A composition according to claim 1, wherein said supple phase is present in said particles in a content of 5% to 99.9% by volume, relative to the total volume of the particle.

42. A composition according to claim 1, wherein said supple phase is present in said particles in a content of at least 10% by volume, relative to the total volume of the particle.

43. A composition according to claim 1, wherein said supple phase is present in said particles in a content of at least 25% by volume, relative to the total volume of the particle.

44. A composition according to claim 1, wherein said supple phase is present in said particles in a content of 25% to 99.9% by volume, relative to the total volume of the particle.

45. A composition according to claim 1, wherein said supple phase is present in said particles in a content of 50% to 95% by volume, relative to the total volume of the particle.

46. A composition according to claim 1, wherein said particles are dispersed in an aqueous medium.

47. A composition according to claim 46, wherein said aqueous medium further comprises a water-miscible solvent.

48. A composition according to claim 47, wherein said water-miscible solvent is chosen from at least one polyol containing from 2 to 8 carbon atoms, $C_2$ to $C_5$ lower monoalcohol, and $C_2$–$C_4$ ketone.

49. A composition according to claim 46, wherein said aqueous medium represents from 5% to 75% by weight, relative to the total weight of the composition.

50. A composition according to claim 46, wherein said aqueous medium represents from 5% to 50% by weight, relative to the total weight of the composition.

51. A composition according to claim 1, wherein said particles are dispersed in a nonaqueous medium that is liquid at 25° C. and atmospheric pressure.

52. A composition according to claim 51, wherein said nonaqueous medium comprises an oil.

53. A composition according to claim 52, wherein said nonaqueous medium comprises a volatile oil.

54. A composition according to claim 53, wherein said volatile oil is chosen from at least one of octamethylcyclotetrasiloxane, decamethylcyclopentasiloxane, hexadecamethylcyclohexasiloxane, heptamethylhexyltrisiloxane, heptamethyloctyltrisiloxane, isododecane, isooctane, isodecane and isohexadecane.

55. A composition according to claim 52, wherein said oil is present in a content from 5% to 97.5% by weight, relative to the total weight of the composition.

56. A composition according to claim 53, wherein said oil is present in a content from 5% to 97.5% by weight, relative to the total weight of the composition.

57. A composition according to claim 54, wherein said oil is present in a content from 5% to 97.5% by weight, relative to the total weight of the composition.

58. A composition according to claim 52, wherein said oil is present in a content from 20% to 75% by weight, relative to the total weight of the composition.

59. A composition according to claim 53, wherein said oil is present in a content from 20% to 75% by weight, relative to the total weight of the composition.

60. A composition according to claim 1, wherein said particles are present in a content ranging from 0.1% to 70% by weight of particle solids relative to the total weight of the composition.

61. A composition according to claim 1, wherein said particles are present in a content ranging from 0.5% to 55% by weight of particle solids, relative to the total weight of the composition.

62. A composition according to claim 1, wherein said particles are present in a content ranging from 1% to 40% by weight of particle solids, relative to the total weight of the composition.

63. A composition according to claim 1, wherein said composition is capable of forming a film having a maximum tensile stress, for a percentage of elongation of less than 100%, of less than or equal to 10 MPa.

64. A composition according to claim 1, wherein said composition is capable of forming a film having a maximum tensile stress, for a percentage of elongation of less than 100%, of 0.1 MPa to 10 MPa.

65. A composition according to claim 1, wherein said composition is capable of forming a film having a maximum tensile stress, for a percentage of elongation of less than 100%, of less than or equal to 5 MPa.

66. A composition according to claim 1, wherein said composition is capable of forming a film having a maximum tensile stress, for a percentage of elongation of less than 100%, of 0.1 MPa to 5 MPa.

67. A composition according to claim 1, wherein it further comprises a dyestuff.

68. A composition according to claim 67, wherein said dyestuff is chosen from at least one of lipophilic dyes, hydrophilic dyes, pigments and nacres.

69. A composition according to claim 67, wherein said dyestuff is present in a proportion of from 0.01% to 50% by weight, relative to the total weight of the composition.

70. A composition according to claim 67, wherein said dyestuff is present in a proportion of from 1% to 30% by weight, relative to the total weight of the composition.

71. A composition according to claim 1, wherein said composition further comprises at least one additive chosen from plasticizers, coalescers, fillers, waxes, pasty fatty substances, surfactants, antioxidants, essential oils, preserving agents, fragrances, neutralizers, emollients, moisturizers, vitamins, essential fatty acids, sunscreens, free-radical scavengers and dispersants.

72. A composition according to claim 1, wherein said composition is in the form of a simple or multiple emulsion containing an oily or aqueous continuous phase, a cream, a gel, a paste, a solid, a mousse, a two-phase or multiphase lotion, or a spray.

73. A composition according to claim 1, wherein said composition is a makeup composition or care composition for the skin and the lips.

74. A composition according to claim 1, wherein said composition is at least one of a foundation, a blusher, a face powder, an eyeshadow, a concealer product, a lipstick, a lip gloss, a lip pencil, an eyeliner or a body makeup product.

75. A composition according to claim 1, wherein said composition is a foundation.

76. A composition according to claim 73, wherein said makeup composition is in the form of a skincare base, an antisun composition, a deodorant or a lipcare product.

77. A composition according to claim 73, wherein said care composition is in the form of a skincare base, an antisun composition, a deodorant or a lipcare product.

78. A cosmetic care process for the skin, comprising applying to the skin a cosmetic composition according to claim 1.

79. A cosmetic makeup process for the skin, comprising applying to the skin a cosmetic composition according to claim 1.

80. A cosmetic care process for the lips, comprising applying to the lips a cosmetic composition according to claim 1.

81. A cosmetic makeup process for the lips, comprising applying to the lips a cosmetic composition according to claim 1.

82. A method of reducing the transfer or deposition of marks from a film of a cosmetic composition applied to the skin onto a support placed in contact with said film, said method comprising the step of applying to the skin said cosmetic composition comprising a dispersion of particles comprising at least one at least partially external supple phase comprising at least one supple polymer having at least one glass transition temperature of less than or equal to 60° C., and at least one at least partially internal rigid phase, the rigid phase being at least one amorphous material having at least one glass transition temperature of greater than 60° C., the supple polymer being at least partially attached by chemical grafting onto the rigid phase.

83. A method of reducing the transfer or deposition of marks from a film of a cosmetic composition applied to the skin onto a support placed in contact with said film, said method comprising the step of applying to the skin said cosmetic composition comprising a dispersion of particles comprising at least one at least partially internal supple phase comprising at least one supple polymer having at least one glass transition temperature of less than or equal to 60° C., and at least one at least partially external rigid phase, the rigid phase being at least one amorphous material having at least one glass transition temperature of greater than 60° C., the supple polymer being at least partially attached by chemical grafting onto the rigid phase.

* * * * *